United States Patent [19]

Kim et al.

[11] Patent Number: 5,215,905
[45] Date of Patent: Jun. 1, 1993

[54] IMMOBILIZATION OF FRUCTOSYLTRANSFERASE ON A BASIC, POROUS ANION-EXCHANGE RESIN

[75] Inventors: Min H. Kim; Sung S. Choi; Man J. In; In S. Choi; Min S. Han; Bun S. Lim, all of Seoul, Rep. of Korea

[73] Assignee: Miwon Co., Ltd., Seoul, Rep. of Korea

[21] Appl. No.: 459,242

[22] Filed: Dec. 29, 1989

[51] Int. Cl.$^5$ .................. C12N 11/08; C12N 9/10; C12P 19/18; C12P 19/04

[52] U.S. Cl. .................. 435/180; 435/97; 435/101; 435/193

[58] Field of Search .......... 435/97, 101, 174, 177, 435/180, 193

[56] References Cited

U.S. PATENT DOCUMENTS

| | | | |
|---|---|---|---|
| 3,708,397 | 6/1973 | Sipos | 195/31 R |
| 3,788,945 | 1/1974 | Thompson et al. | 195/31 F |
| 3,850,751 | 11/1974 | Messing | 195/63 |
| 3,868,304 | 2/1975 | Messing | 195/31 F |
| 4,239,854 | 12/1980 | Hirohara et al. | 435/180 X |
| 4,356,262 | 10/1982 | Heady | 435/97 |
| 4,390,626 | 6/1983 | Chibata et al. | 435/180 X |
| 4,617,269 | 10/1986 | Rathbone et al. | 435/193 X |
| 4,818,695 | 4/1989 | Eigtved | 435/180 X |

FOREIGN PATENT DOCUMENTS

| | | |
|---|---|---|
| 0132998 | 2/1985 | European Pat. Off. |
| 1482122 | 8/1977 | United Kingdom |
| 2000144 | 1/1979 | United Kingdom |

OTHER PUBLICATIONS

The Merck Index, Eleventh Edition, Published by Merck & Co., Inc., Rahway, NJ, U.S.A., p. 702 (1989).

*Primary Examiner*—David M. Naff
*Attorney, Agent, or Firm*—Birch, Stewart, Kolasch & Birch

[57] ABSTRACT

An immobilized fructosyltransferase enzyme is prepared by providing a porous or macroporous anion exchange resin having at least 1.0 m$^2$/g of internal surface, at least 0.1 ml/g of total porous volume, a spherical radius of 20–2,000 angstroms, and a nominal ion-exchange capacity of at least 1.0 meq./g of wet resin, adding to the ion-exchange resin a solution of fructosyltransferase enzyme derived from a microorganism of the genus Aureobasidium, Aspergillus, Fusarium, or Gloeosporium at a pH value of about 3–8, filtering and wind-drying the absorbed resin, and storing it in a cool place. A bifunctional cross-linking agent may be present in the solution of fructosyltransferase enzyme.

6 Claims, 2 Drawing Sheets

IMMOBILIZATION OF FRUCTOSYLTRANSFERASE ON A BASIC, POROUS ANION-EXCHANGE RESIN

BACKGROUND OF THE INVENTION

1. Field of the Invention

The present invention relates to an immobilized fructosyltransferase enzyme and a process for the preparation thereof and more particularly, to a method for the production of an immobilized fructosyltransferase enzyme in which an effective amount of the enzyme obtained from a microorganism which is of the genus Aureobasidium, Aspergillus, Fusarium, or Gloeosporium, is immobilized on an ion-exchange resin carrier, which is a porous or macroporous, basic anion exchange resin, at a pH between about 3 and 8, preferably at a pH between 4 and 6, which may be optionally combined with a bifunctional crosslinking agent and a buffer solution with a concentration in the enzyme solution of 0.01 to 0.1M. preferably 0.025–0.075M and wherein 1 mg of the enzyme protein is suspended in 0.01 to 0.15 milli mol equivalent (hereafter "meq."), preferably 0.025 to 0.1 meq., more preferably 0.05–0.1 meq. of the ion-exchange resin, whereby the immobilized fructosyltransferase enzyme can be used to produce fructooligosaccharide in high yield.

2. Description of the Prior Art

A preferred fructosyltransferase enzyme useful in the practice of the present invention is derived from the genus Aureobasidium, Aspergillus, Fusarium, or Gloeosproium as disclosed in U.S. Pat. No. 4,356,262 and U.K. Patent 2,000,144. Such fructosyltransferase, upon reacting with a sucrose solution, converts the sucrose to fructooligosaccharide. The structure of the fructooligosaccharide is such that 1–4 fructose units are combined with a sucrose at the $\beta(1-2)$ position of the sugar and its uses include accelerating the activity of Bifidus in the intestines, and use as a sweetening agent which does not readily cause tooth decay, and is low in calories. Fructooligosaccharides have been produced by immobilized fructosyltransferase using the species Polyacrylamide, Carragaenan, or Alginate. However, such immobilization matrices have suffered from many problems such as, for example: (1) It is difficult to retain extracellular enzyme, (2) internal mass transfer resistance is relatively large, (3) the physical rigidity is weak, (4) the matrix itself can be decomposed by microorganisms over a period of time, and (5) it is difficult to mass-produce the bead.

Recently, in an attempt to avoid such problems and disadvantages, the enzyme glucose isomerase was immobilized on a water-insoluble inert carrier to convert glucose into fructose as described in U.S. Pat. Nos. 3,708,397, 3,788,945, 3,850,751, 3,868,304, and U.K. Patent 1,482,122. However, these patents do not disclose the use of an basic, anion-exchange resin having at least 1.0 m²/g of internal surface, at least 0.1 ml/g of total porous volume, a radius of 20–2,000 angstroms, and an nominal capacity of at 1.0 meq./g of wet resin for efficiently producing an active and stable fructosyltransferase enzyme.

SUMMARY OF THE INVENTION

Accordingly, it is an object of the present invention to provide immobilized fructosyltransferase enzyme and an improved process for the preparation thereof.

Another object of the present invention is to provide a method for the production of an immobilized fructosyltransferase enzyme which includes immobilizing the enzyme from the genus Aureobasidium, Aspergillus, Fusarium or Gloeosporium on an ion-exchange resin carrier which is porous and strongly basic, anion-exchangeable at a pH between 3 and 8, preferably at a pH between 4 and 6, and which may be optionally combined with a bifunctional crosslinking agent.

The concentration of buffer species in the enzyme solution is 0.01–0.1M preferably 0.025–0.075M wherein 1 mg of enzyme protein is dissolved per 0.01–0.15 meq., preferably 0.025–0.1 meq., more of the ion-exchange resin. The resin-absorbed immobilized fructosyltransferase enzyme obtained thereby can be used to produce fructooligosaccharides in high yield stably.

A further object of the present invention is to efficiently provide an immobilized fructosyltransferase enzyme which exhibits sufficient activity and stability, and is inexpensive to prepare. The immobilized enzyme therefore allows for reuse of the enzyme and prevents the product from being decomposed by microorganisms Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

Briefly described, the present invention relates to a process for the preparation of an immobilized fructosyltransferase enzyme which comprises the steps of (a) providing an ion-exchange resin having at least 1.0 m²/g of internal surface, at least 0.1 ml/g of a total porous volume, at least a spherical radius of 20–2,000 angstroms, and an activity of at least 1.0 meq./g of wet resin, (b) adding to the ion-exchange resin from step (a) a solution of fructosyltransferase enzyme derived from the genus Aureobasidium, Aspergillus, Fusarium, or Gloeosporium at a pH value of about 3–8, so as to immobilize the enzyme on the ion-exchange resin by ionic bonding, (c) filtering the enzyme absorbed on the ion-exchange resin from step (b) to produce the immobilized fructosyltransferase enzyme, and (d) wind-drying the filtrate from step (c) and storing in a cool place.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENTS

Figure 1:
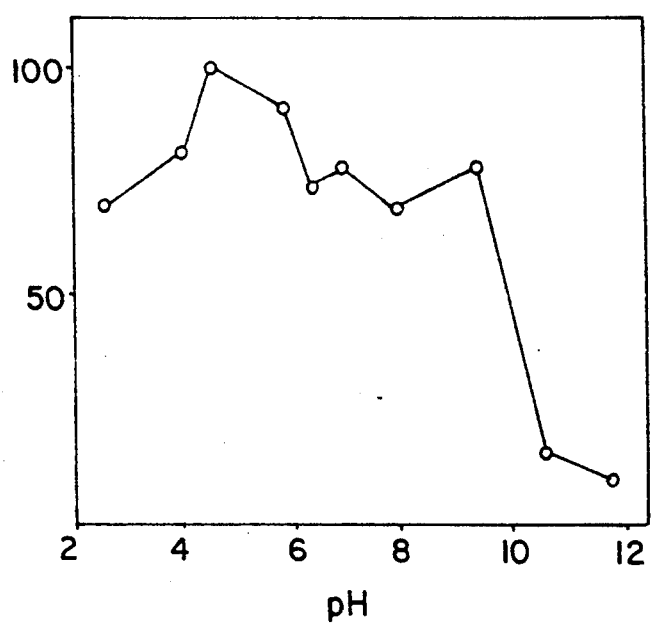
FIG. 1 illustrates the activity of the immobilized enzyme at various pH values according to the present invention.

Referring now in detail to the drawings for the purpose of illustrating preferred embodiments of the present invention, there is provided an immobilized fructosyltransferase enzyme having high activity and stability and a process for its manufacture.

The present invention is directed to a process for the preparation of the immobilized fructosyltransferase enzyme which includes the steps of (a) providing an insoluble, porous or macroporous, basic anion-exchange resin having at least 1.0 m²/g of internal surface, at least 0.1 ml/g of a total porous volume, at least a spherical radius of 20 to 2,000 angstroms, and a nominal capacity of at least 1.0 meq./g of wet resin, (b) applying to the ion-exchange resin from step (a) a solution of fructosyltransferase enzyme derived from the genus Aureobasidium, Aspergillus, Fusarium, or Gloeosporium at a pH value of from about 3-8 so as to immobilize the enzyme on the ion-exchange resin, (c) filtering the ion-exchange resin from step (b) to produce the wet immobilized fructosyltransferase enzyme, and (d) wind drying the wet immobilized enzyme from step (c) and storing obtained enzyme in a cool place at a temperature of 4° C.

Examples of the ion-exchange resin in step (a) included is Diaion PA412, WA30, HPA25, Amberlite IRA904, IRA93, Dowex WSAI, Duolite A7, and the like.

In step (b), the enzyme activity and stability were affected by (1) pH value, (2) ion concentration in the enzyme solution, (3) relative amount of ion-exchange resin to be contacted to that of enzyme, and (4) cross-linking agent reaction properties. The optional cross-linking agent which may be used in step (b) includes glutaraldehyde, succinaldehyde, or malondialdehyde and it is added to the ion-exchange resin in an amount of from 0.01 to 0.1% (v/v) of the final concentration of the mixed solution of step (b), at a temperature of 4° to 10° C. for 10 to 20 hours It showed slight deactivation of the enzyme but it was found to increase the enzyme activity by 5-10% after storing for 40 days, compared to the control.

Also, in step (b), a buffer solution is used with a concentration in the enzyme solution of 0.01 to 0.1M, preferably 0.025 to 0.075, in 0.01 to 1.15 meq. preferably 0.025 to 0.1 meq. more of the ion-exchange resin.

According to the present invention, the enzyme activity is measured as follows:

First of all, a buffer solution of 0.05M of citric acid or acetic acid having a pH of 5.5, and 0.5 g of the immobilized fructosyl enzyme is added to a 60% (w/v) sucrose solution at a temperature of 60° C. for 30 minutes to produce a reducing sugar. An amount of the obtained reducing sugar is calculated by the DNS (2-4-dinitrosalicylic acid) method in which the 1 unit of measurement is the ability to produce 1 μm of reducing sugar per 1 minute.

The amount of the oligosaccharide is calculated by the conversion from sucrose to the oligosaccharide as follows:

$$\text{conversion rate (\%)} = \frac{\text{concentration of oligosaccharide formed on output}}{\text{concentration of sucrose on input}} \times 100$$

The buffer solution is made with 0.01-0.1M of citric acid or acetic acid with the enzyme solution.

As shown in FIGS. 1-4, the enzyme activity is highest at a pH value between 4 and 6, and is good at a pH value between 3 and 8 (FIG. 1).

Figure 2:
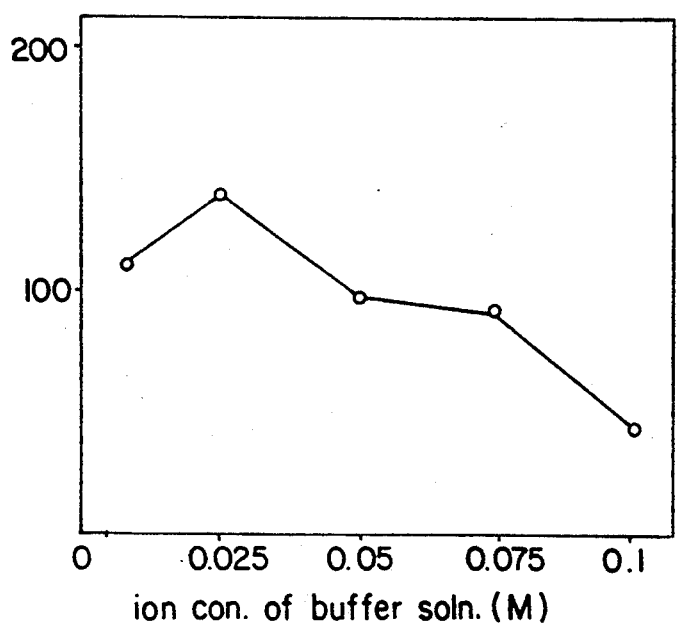
FIG. 2 illustrates the activity of the immobilized enzyme depending on the ion concentrations of the enzyme solution according to the present invention.

The buffer concentration range of enzyme solution which yielded the highest immobilized fructosyltransferase activity is 0.01-0.1M. However, near the lower range of buffer concentration, buffering function was not sufficient that pH changed during immobilization (FIG. 2).

Figure 3:
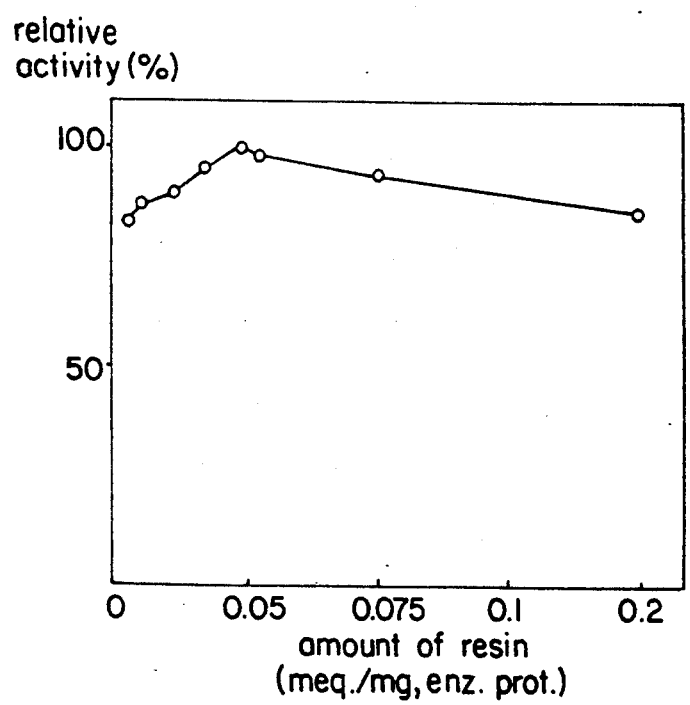
FIG. 3 illustrates the activity of the immobilized enzyme depending on the amount of ion-exchange resin according to the present invention.

A proper amount of charged ion-exchange resin is 0.05-0.1 meq. of ion-exchange per 1 mg of enzyme protein (FIG. 3).

Figure 4:
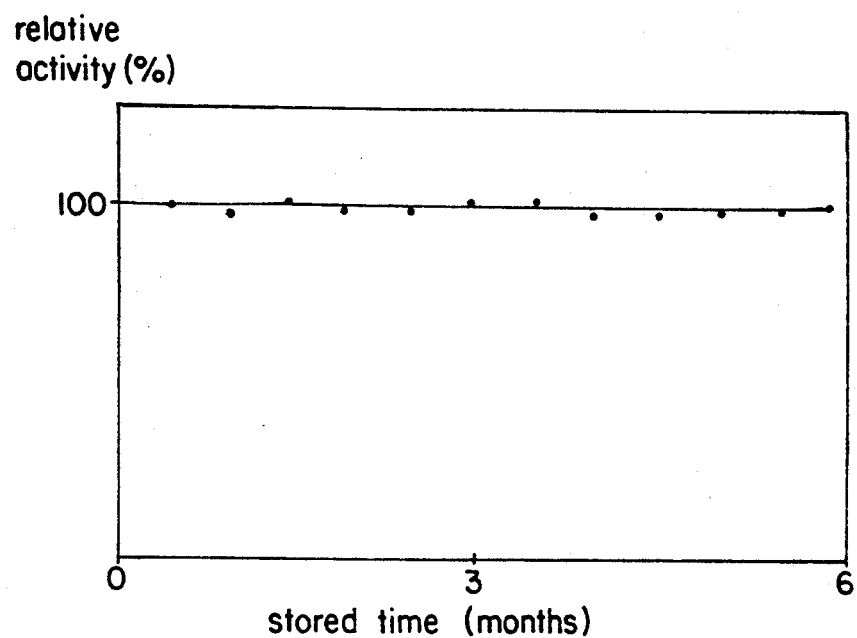
FIG. 4 illustrates the change in activity of the immobilized enzyme depending on the storage period of wind-dried, immobilized enzyme according to the present invention.

The dried immobilized enzyme did not change any activity thereof when stored in a cool place at 4° C. for six months (FIG. 4).

The fructosyltransferase enzyme according to the present invention possess specific properties as follows:

(1) The enzyme protein is immobilized on the ion-exchange resin at a ratio of 1:2 of absorbed protein concentration (mg/ml) per non-absorbed protein raffinate concentration (mg/ml) thereof, (2) productivity of fructooligosaccharides using the present invention is high, due to the high retention of specific activity and low mass transfer resistance, (3) since the processes are simple, the enzyme can be mass produced, (4) the enzyme can be maintained for 40 days since the stability thereof is excellent, and (5) the enzyme can be stored for more than six months when the enzyme is dried with negligible loss of activity.

The present invention will now be described in more detail in connection with the following examples which should be considered as being exemplary and not limiting the present invention.

EXAMPLE 1

5 g of acidic and basic ion-exchange resins which are equivalent to nominal capacity range of 4.7-12.5 meq. depending on resin types were mixed with 100 ml of enzyme solution at 30° C. for 12 hours. The content of protein and citrate in the enzyme solution was 200 mg and 2.5 mmole, respectively. During filtration 100 ml of deionized water was added to wash out the non-adsorbed protein. The obtained immobilized enzyme showed the properties set forth in Table I.

EXAMPLE 2

A basic ion-exchange resin supplied as a 10 g unit mixes with fructosyltransferase enzyme as in Example 1. The enzyme absorbed resin is filled in a column of 10 mm×200 mm at a pH value of 5.5, and 60% (w/v) sucrose solution was added thereto as 1.5 (hour)$^{-1}$ of space velocity. Thereafter, the operational stability, as set forth in Table II, was observed.

EXAMPLE 3

Gel and porous basic ion-exchange resin supplied as a 10 g unit are mixed with fructosyltransferase enzyme as in Example 1. Glutaraldehyde was added so as to maintain 0.05% (v/v) thereof and agitated at 10° C. for 12 hours with 80-100 rpm. After filtering, the ion-exchange resin was washed with 1 liter of deionized water. The obtained immobilized enzyme was filled in a column which was maintained at a pH of 4-5 and 50-60% (v/v) sucrose solution was put into the column with 1.5 (hours)$^{-1}$ of space velocity. After for 40 days of operation, the enzyme in the column showed the following stability as in Table III.

TABLE I

| type | | ion-exchange resin | amount of enzyme absorption (units/g of wet resin) |
|---|---|---|---|
| Strongly acidic cation | gel | Diaion SK 1B | trace |
| | porous | Diaion PK 204 | " |
| | " | Amberlite IRA 124 | " |
| Weakly acidic cation | " | Diaion WK 10 | " |
| | " | Diaion WK 20 | " |
| | " | Diaion WK 11 | " |
| Strongly basic anion | gel | Diaion SA 11A | " |
| | " | Amberlite IRA 400 | " |
| | porous | Diaion PA 304 | 11.0 |
| | " | Diaion PA 320 | 25.2 |
| | " | Diaion PA 412 | 38.5 |
| | " | Diaion HPA 25 | 44.6 |
| | " | Amberlite IRA 410 | 35.0 |
| | " | Amberlite IRA 404 | 33.3 |
| | " | Amberlite IRA 904 | 45.8 |
| | " | Amberlite IRA 900 | 40.7 |
| | " | Dowex MSA 1 | 51.0 |
| Weakly basic anion | gel | Diaion WA11 | 1.6 |
| | " | Diaion WA20 | 2.0 |
| | " | Amberlite IRA45 | 9.7 |
| | porous | Diaion WA30 | 46.4 |
| | " | Amberlite IRA93 | 50.6 |

TABLE II

| Ion-exchange resin | Duration of operation (55% conversion to oligosaccharide) | Half life (days) |
|---|---|---|
| PA 304 | 30 | 42 |
| PA 412 | 33 | 48 |
| IRA 404 | 30 | 40 |
| IRA 400 | 29 | 40 |
| IRA 900 | 35 | 50 |
| IRA 904 | 37 | 52 |
| IRA 93 | 36 | 52 |
| HPA 25 | 38 | 50 |
| MSA 1 | 40 | 55 |

TABLE III

| Type | ion-exchange resin | % remaining activity around 40 days | |
|---|---|---|---|
| | | non-treatment | treatment |
| gel | Duolite A101D | 5.0 | None |
| | Diaion WA 20 | 4.3 | " |
| | Diaion SA 11 | 3.7 | " |
| porous | Amberlite -IRA 904 | 61.4 | 67.0 |
| | Dowex MSA 1 | 66.3 | 71.6 |
| | Diaion 412 | 57.8 | 62.4 |

EXAMPLE 4

Fructosyltransferase enzyme was fixed on a porous basic anion exchange resin as in Example 1 to produce an immobilized enzyme. After the wet enzyme was dried outside in the wind, it was stored in a cool place at 4° C. and there was no change in enzyme activity for 6 months (FIG. 4).

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for the preparation of an immobilized fructosyltransferase enzyme which comprises the steps of:
   (a) providing a basic and porous anion-exchange resin having at least 1.0 m$^2$/g of internal surface, at least 0.1 ml/g of total porous volume, a spherical radius of 20–2,000 angstroms, a nominal ion-exchange capacity of at least 1.0 meq./g of wet resin,
   (b) applying to said anion-exchange resin from step (a) a solution of fructosyltransferase enzyme derived from the genus Aureobasidium, Aspergillus, Fusarium, or Gloeosporium at a pH value of about 3–8 such that said anion-exchange resin is present in the solution of the enzyme at a ratio of about 0.025–0.1 meq. to about 1 mg of enzyme protein of said enzyme solution, so as to immobilize the enzyme on said anion-exchange resin, said solution of fructosyltransferase enzyme including a bifunctional crosslinking agent and about 0.025–0.075M of buffer solution,
   (c) filtering said enzyme immobilized of said anion-exchange resin from step (b) to produce a wet immobilized fructosyltransferase enzyme, and
   (d) wind drying the immobilized fructosyltransferase enzyme from step (c) and storing in a cool place at a temperature of about 4° C.

2. The process of claim 1, wherein the anion-exchange resin is microporous.

3. The process of claim 1, wherein the pH value is about 4–6.

4. The process of claim 1, wherein the buffer solution is a solution of an acid selected from the group consisting of acetic acid and citric acid.

5. The process of claim 1, wherein the bifunctional crosslinking agent is selected from the group consisting of succinaldehyde and malondialdehyde.

6. The process of claim 1, wherein said crosslinking agent is glutaraldehyde maintained at 0.01–0.1% (v/v) of the final concentration of the mixed solution of step (b).

* * * * *